United States Patent [19]
Naito et al.

[11] 3,960,833
[45] June 1, 1976

[54] BUTIROSIN A 3'',5''-O-ISOPROPYLIDENE DERIVATIVES

[75] Inventors: Takayuki Naito; Susumu Nakagawa, both of Tokyo; Soichiro Toda, Koshigaya, all of Japan

[73] Assignee: Bristol-Myers Company, New York, N.Y.

[22] Filed: Jan. 29, 1975

[21] Appl. No.: 544,994

Related U.S. Application Data

[63] Continuation-in-part of Ser. No. 527,983, Nov. 29, 1974, abandoned.

[52] U.S. Cl............................ 260/210 AB; 424/180
[51] Int. Cl.$^2$........................................ C07H 15/22
[58] Field of Search................... 260/210 AB, 210 R

[56] References Cited
UNITED STATES PATENTS

| | | | |
|---|---|---|---|
| 3,792,037 | 2/1974 | Kawaguchi et al. | 260/210 AB |
| 3,826,802 | 7/1974 | Kawaguchi et al. | 260/210 AB |

*Primary Examiner*—Johnnie R. Brown
*Attorney, Agent, or Firm*—Robert E. Havranek

[57] ABSTRACT

3'-Deoxybutirosin A (3'-deoxyambutyrosin A), which is prepared from butirosin A, possesses an improved antibacterial spectra, especially against butirosin A resistant organisms.

2 Claims, No Drawings

BUTIROSIN A 3'',5''-O-ISOPROPYLIDENE DERIVATIVES

CROSS-REFERENCE TO RELATED APPLICATIONS

This application is a continuation-in-part of copending application Ser. No. 527,983 filed Nov. 29, 1974, now abandoned.

BACKGROUND OF THE INVENTION

1. Field of the Invention

This invention relates to a semi-synthetic derivative of butirosin A, said compound being prepared by dehydroxylation of the 3'-position of butirosin A.

2. Description of the Prior Art

The starting material for the preparation of the compound of the instant invention is butirosin A, also known as ambutyrosin A. It is described and claimed in U.S. Pat. No. 3,541,078 which issued Nov. 17, 1971, and it has the formula

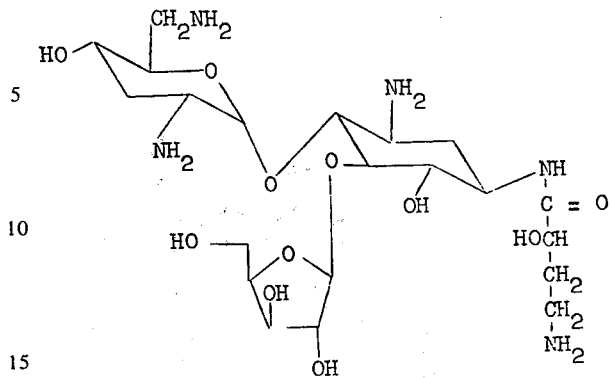

or a nontoxic pharmaceutically acceptable acid addition salt thereof is a valuable antibacterial agent.

This invention relates to a semi-synthetic derivative of butirosin A, said compound being known as 3'-deoxybutirosin A and having the formula

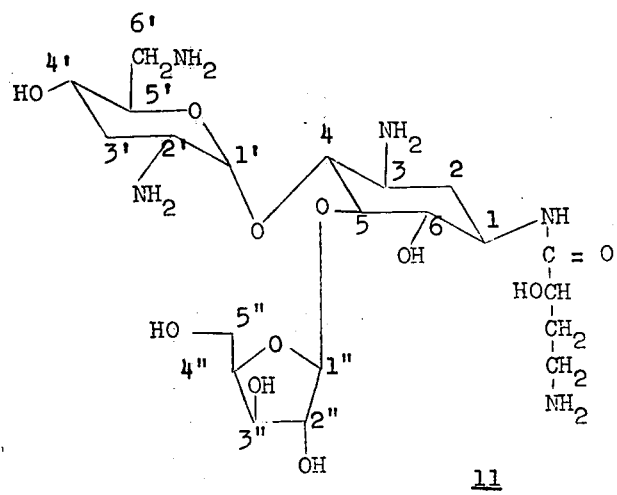

or a nontoxic pharmaceutically acceptable acid addition salt thereof.

For the purpose of this disclosure, the term "nontoxic pharmaceutically acceptable acid addition salt" shall mean a mono, di-, tri- or tetrasalt formed by the interaction of 1 molecule of compound 11 with 1–4 moles of a nontoxic, pharmaceutically acceptable acid. Included among these acids are acetic, hydrochloric, sulfuric, maleic, phosphoric, nitric, hydrobromic, ascorbic, malic and citric acid, and those other acids commonly used to make salts of amine containing pharmaceuticals.

Also for the purpose of this disclosure the term (lower)alkyl, (lower)alkoxy or (lower)alkanol shall mean a radical containing 1 to 6 carbon atoms.

SUMMARY OF THE INVENTION

The compound having the formula

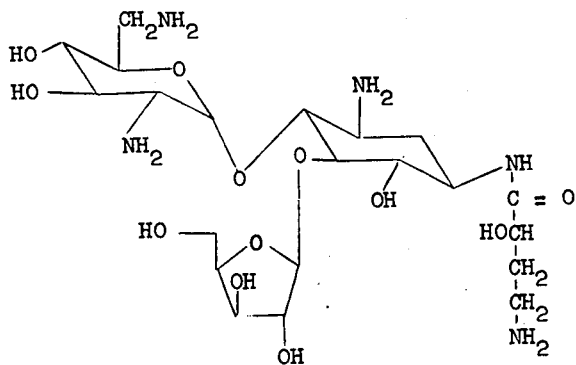

The compounds of the present invention are prepared by the following diagramatic scheme:

Diagram 1
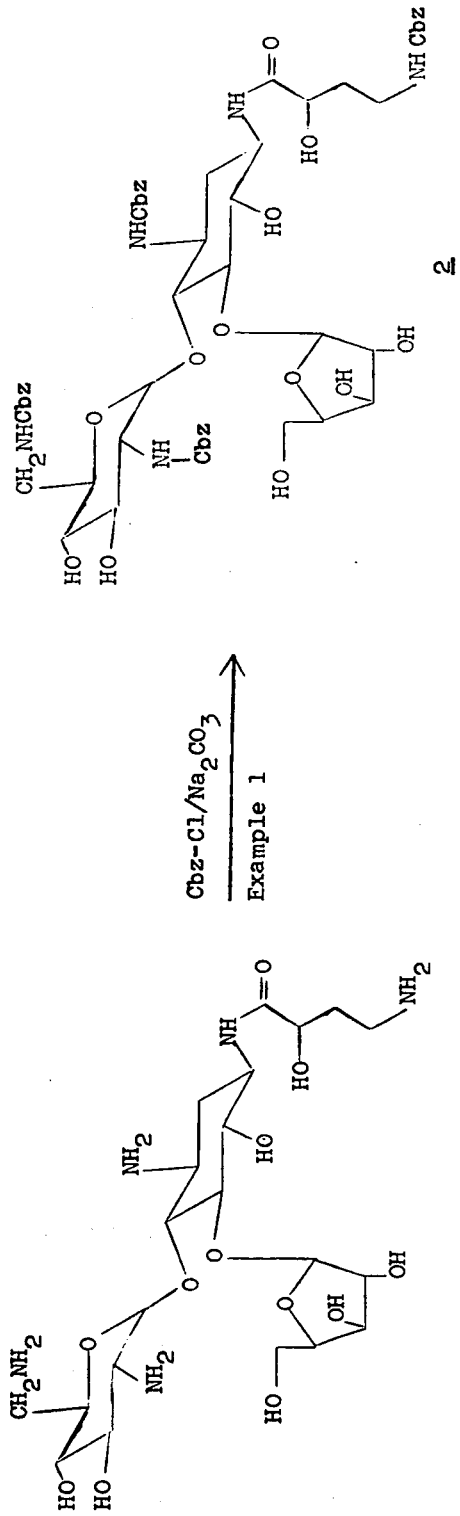
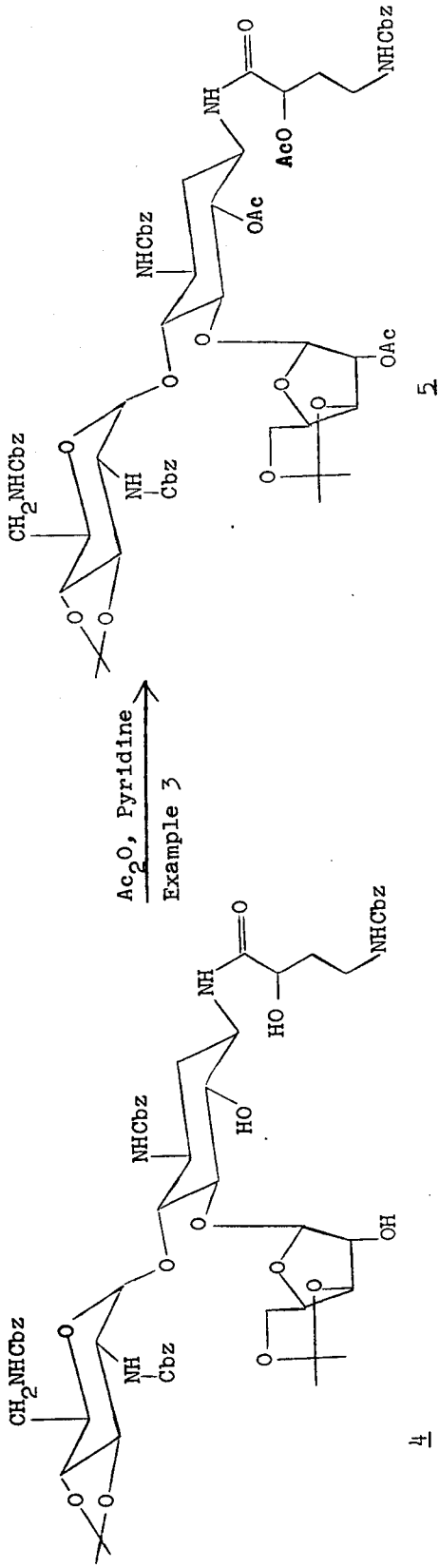

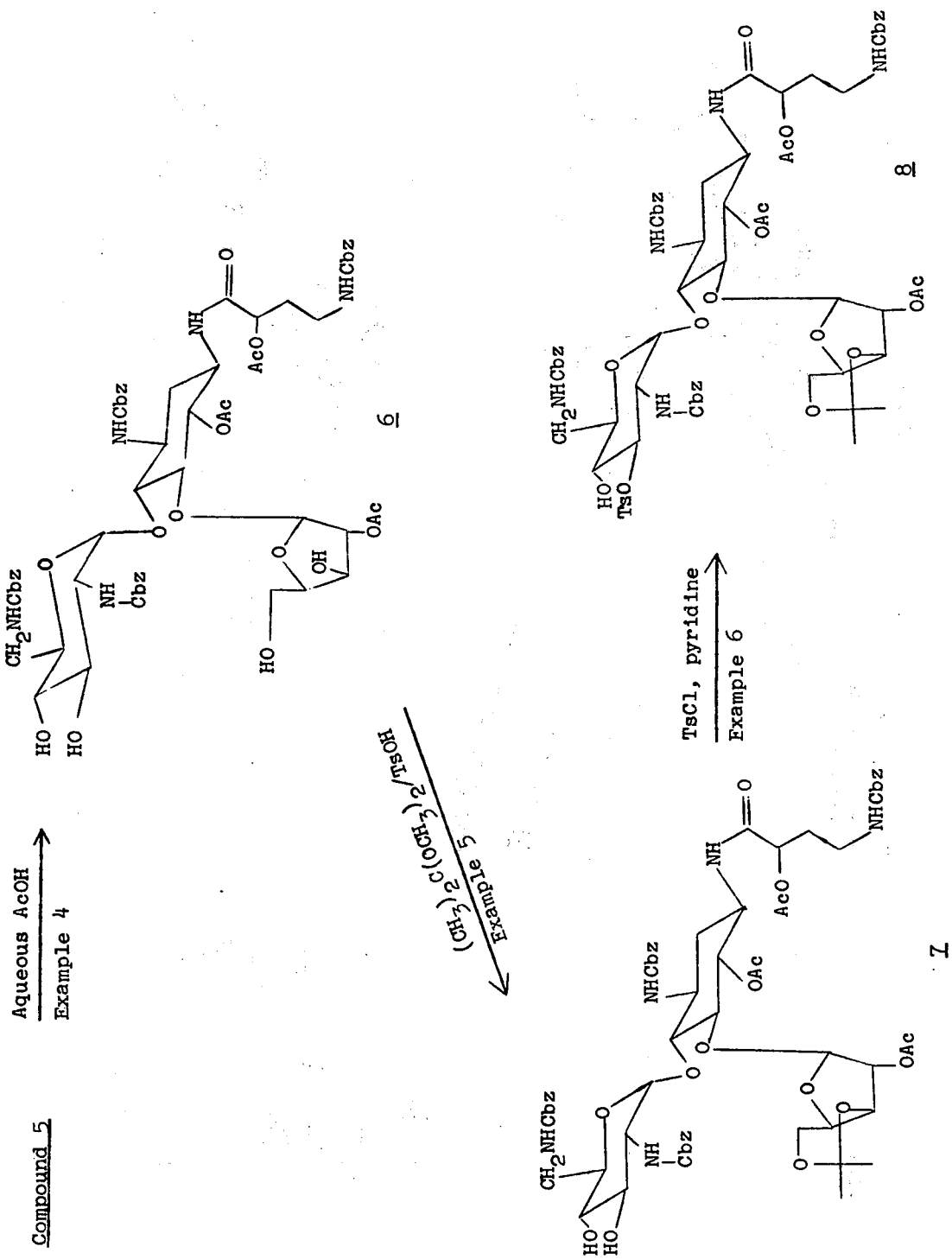

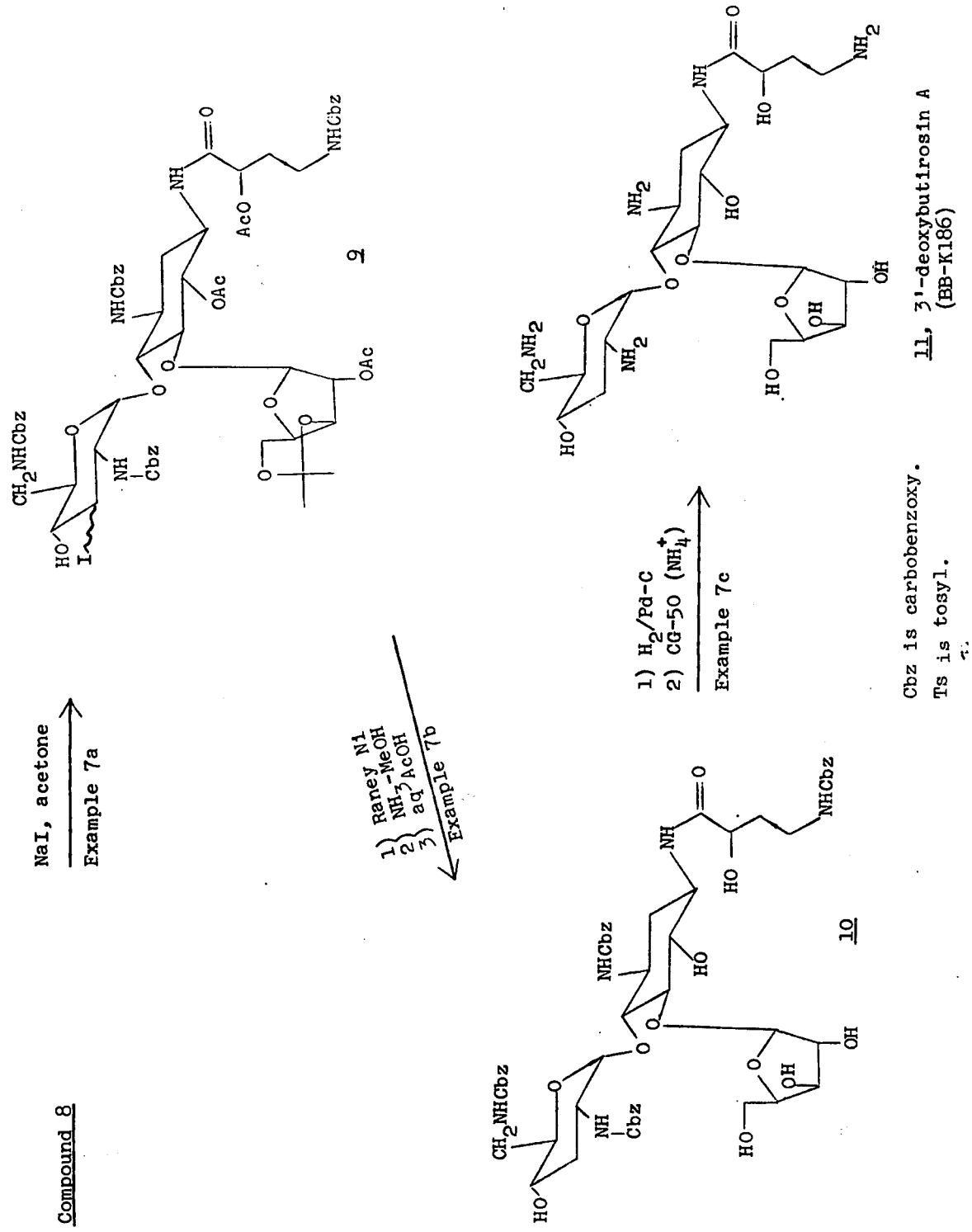

A preferred embodiment of the present invention is the compound having the formula

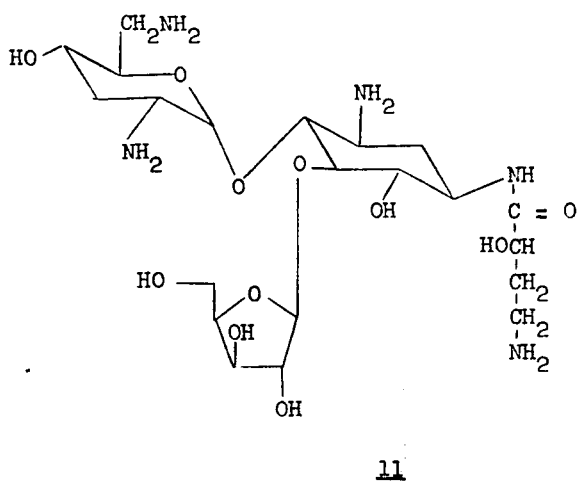

11 or a pharmaceutically acceptable nontoxic salt thereof.

A most preferred embodiment is the mono- or disulfate salt of the compound 11.

A most preferred embodiment is the mono- or polyhydrate of the compound 11.

A most preferred embodiment is the mono- or polyhydrate of the disulfate salt of compound 11.

The objectives of the present invention have been achieved, by the provision according to the present invention of the process for the preparation of the compound having the formula

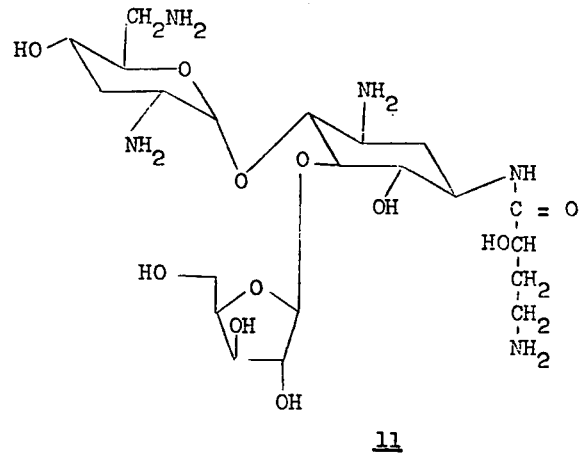

11 from butirosin A which process is characterized by the step of treating the compound having the formula

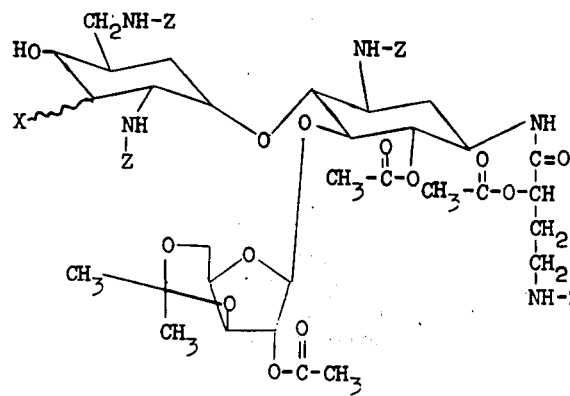

9 in which Z is a radical having the formula

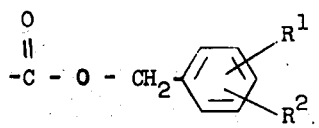

in which $R^1$ and $R^2$ are alike or different and are (lower)alkyl or (lower)alkoxy of 1 to 3 carbon atoms, Cl, Br, F, hydroxy, nitro, $CF_3$ or $SO_3H$, and X is acylthio, Br or I, with hydrogen in the presence of Raney nickel to produce the compound having the formula

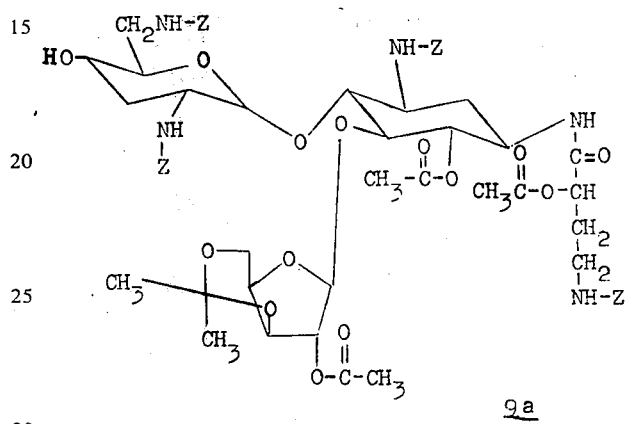

9a in which Z is as defined above.

Another preferred embodiment is the process for the preparation of the compound having the formula:

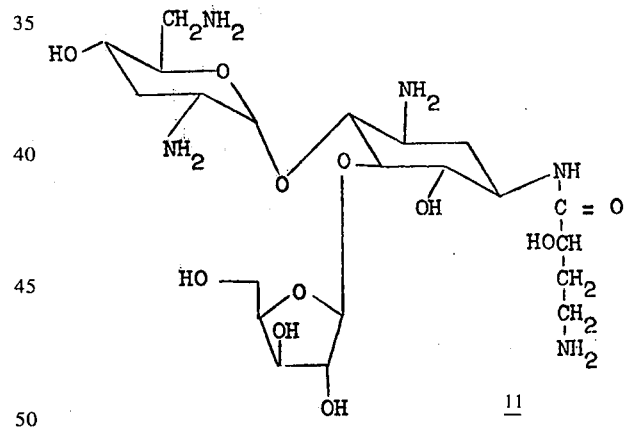

11 from butirosin A which process is characterized by the steps of

A. treating the compound having the formula

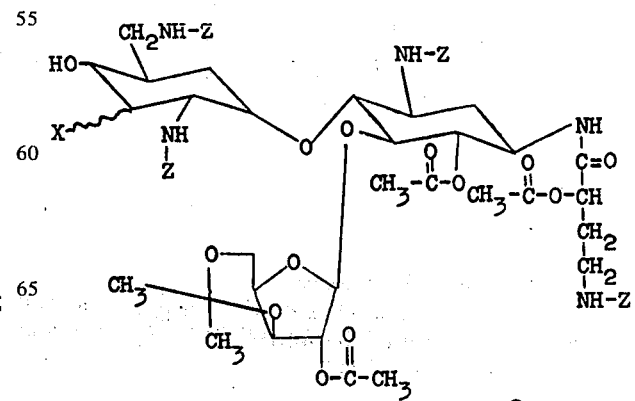

9 in which Z is a radical having the formula

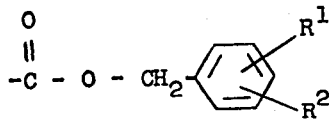

in which $R^1$ and $R^2$ are alike or different and are hydrogen, (lower)alkyl or (lower)alkoxy of 1 to 3 carbon atoms, Cl, Br, F, hydroxy, nitro, $CF_3$ or $SO_3H$, and X is acylthio, Br or I, with hydrogen in the presence of Raney nickel to produce the compound having the formula

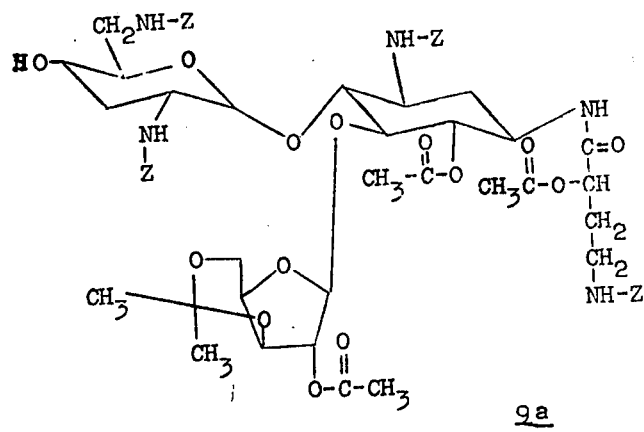

in which Z is as defined above;

B. treating compound 9a with ammonia dissolved in a (lower)alkanol, followed by removal of the solvent to product compound 9b having the formula

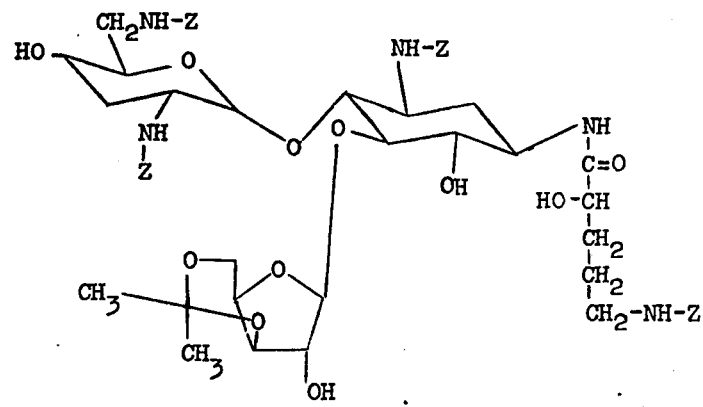

in which Z is as defined above;

C. treating compound 9b with aqueous acetic acid, followed by removal of the solvent to produce compound 10 having the formula

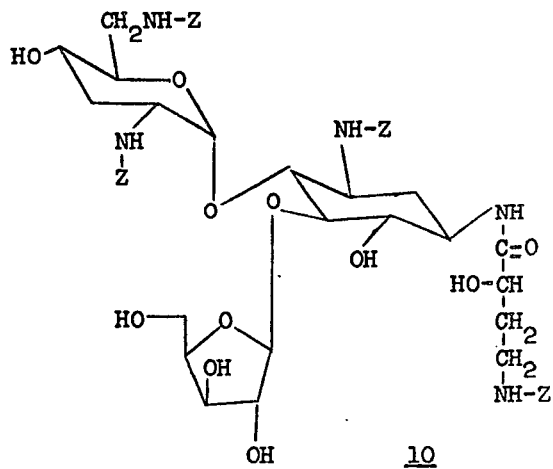

in which Z is as above; and

D. hydrogenating compound 10 with hydrogen in the presence of a metal catalyst in a solvent to produce compound 11.

A most preferred embodiment is the process for the preparation of compound 11 which process is characterized by the consecutive steps of A. treating the compound having the formula

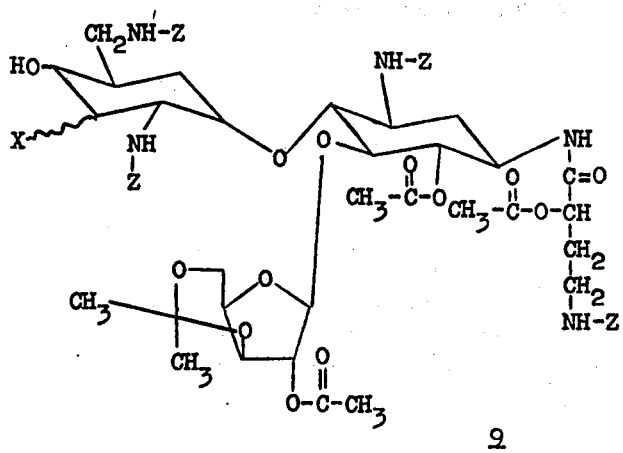

2 in which Z is a radical having the formula

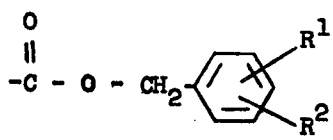

in which $R^1$ and $R^2$ are alike or different and are hydrogen, (lower)alkyl or (lower)alkoxy of 1 to 3 carbon atoms, Cl, Br, F, hydroxy, nitro, $CF_3$ or $SO_3H$, and X is Br or I, with hydrogen in the presence of Raney nickel in a solvent system selected from the group consisting of dioxane, tetrahydrofuran, (lower)alkanols, or mixtures thereof with water, to produce the compound having the formula

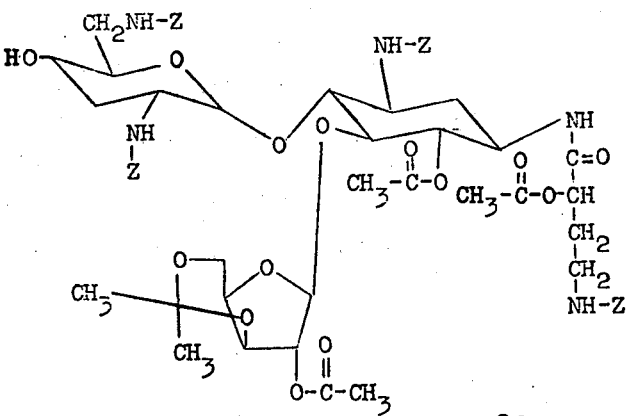

in which Z is as defined above;

B. treating compound 9a with at least 5% ammonia dissolved in a (lower)alkanol for at least 30 minutes at room temperature, followed by removal of the solvent in vacuo to produce compound 9b having the formula

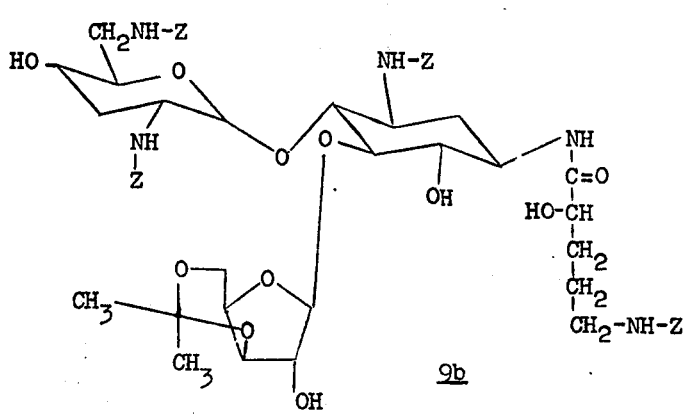

in which Z is as defined above;

C. treating compound 9b with at least 30% aqueous acetic acid, with the aid of heat, for at least one hour, followed by removal of the solvent in vacuo to produce compound 10 having the formula

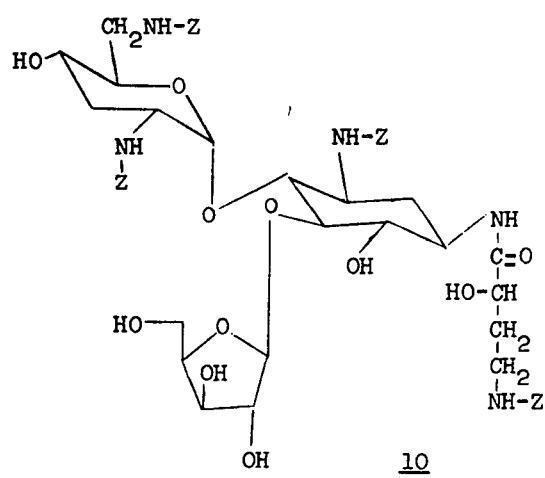

in which Z is as above; and

D. hydrogenating compound 10 with hydrogen in the presence of a metal catalyst selected from the group consisting of platinum, palladium, palladium on charcoal, nickel and ruthenium, in a solvent system selected from the group consisting of water, tetrahydrofuran, dioxane, a (lower)alkanol, or mixtures thereof, without or in the presence of a small amount of an amine selected from the group consisting of triethylamine, pyridine, dicyclohexylamine, diisopropylamine, dimethylaniline and N-methylpiperidine to produce compound 11.

Another preferred embodiment is the compound having the formula

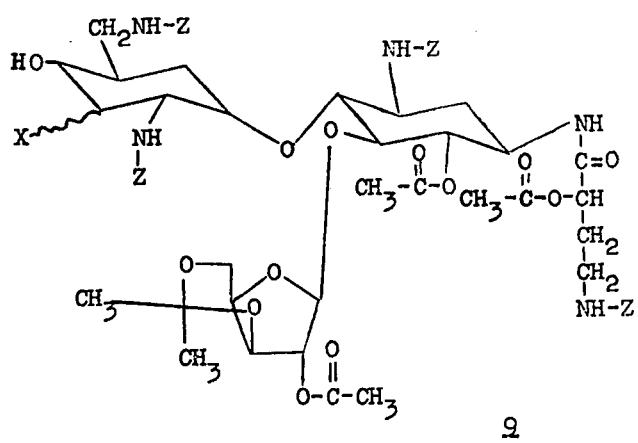

in which Z is a radical having the formula

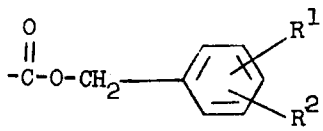

in which $R^1$ and $R^2$ are alike or different and each are hydrogen, chloro, bromo, fluoro, hydroxy, nitro, $CF_3$, $SO_3H$, (lower)alkyl of 1 to 3 carbon atoms or (lower)alkoxy of 1 to 3 carbon atoms and X is iodo or bromo.

A most preferred embodiment is the compound 9 in which Z is

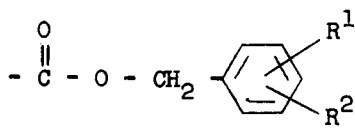

and X is iodo.

Compound 11, 3'-deoxybutirosin A (BB-K186), possesses good antibacterial activity that in many respects is superior to butirosin A itself and in some respects superior to 4'-deoxybutirosin A, also known in the art as Bu-1975$C_1$. Illustrated below is a table showing the minimal inhibitory concentrations (MIC's) of butirosin A, 4'-deoxybutirosin A and compound 11 (BB-K186) against a variety of gram-positive and gram-negative bacteria as obtained by the Steers agar-dilution method on Mueller-Hinton medium.

Table I

| Organisms | | MIC (mcg/ml) BB-K 186 "3'-deoxy-butirosin A" | Bu-1975$C_1$ "4'-deoxy-butirosin A" | Bu-1709$A_1$ "butirosin A" |
|---|---|---|---|---|
| E. coli | NIHJ | 1.6 | 1.6 | 1.6 |
| " | PO1495 | 1.6 | 1.6 | 1.6 |
| " | ML1630 | 3.1 | 3.1 | 3.1 |
| " | NR79/W677 | >100 | >100 | >100 |
| " | JR35/C600 | 0.8 | 0.8 | 0.8 |
| " | A20107 | 3.1 | 3.1 | 50 |
| " | JR66/W677 | 3.1 | 6.3 | 100 |
| " | R5 | 3.1 | 3.1 | 3.1 |
| " | A20895 | 3.1 | 3.1 | 3.1 |
| " | A20732 | 1.6 | 1.6 | 1.6 |

Table I -continued

| Organisms | | BB-K 186 "3'-deoxy-butirosin A" | MIC (mcg/ml) Bu-1975C₁ "4'-deoxy-butirosin A" | Bu-1709A₁ "butirosin A" |
|---|---|---|---|---|
| K. pneumoniae | D11 | 0.8 | 0.8 | 0.8 |
| " | 22-3038 | 3.1 | 6.3 | >100 |
| Ent. cloacae | A20364 | 1.6 | 3.1 | 1.6 |
| " | A21006 | 3.1 | 6.3 | >100 |
| Pr. vulgaris | A9436 | 0.4 | 0.8 | 0.4 |
| Pr. morganii | A20031 | 3.1 | 3.1 | 1.6 |
| Pr. mirabilis | A9554 | 1.6 | 1.6 | 1.6 |
| Prov. stuartii | A20894 | 25 | >100 | >100 |
| Ps. aeruginosa | A9930 | 0.8 | 1.6 | 6.3 |
| " | A20635 | 25 | >100 | >100 |
| " | No. 130 | 12.5 | 25 | 25 |
| " | A20601 | 12.5 | 25 | 50 |
| " | A20896 | 50 | 50 | >100 |
| " | GN-315 | >100 | >100 | >100 |
| Pseudomonas sp. | A20621 | 100 | >100 | 100 |
| Ser. marcescens | A20019 | 6.3 | 6.3 | 6.3 |
| " | A21247 | 3.1 | 6.3 | 6.3 |
| S. aureus | Smith | 0.8 | 1.6 | 0.8 |
| " | D193 | 1.6 | 3.1 | 3.1 |
| " | D133 | 3.1 | 6.3 | 6.3 |
| " | D137 | 12.5 | 25 | 25 |
| " | A20239 | 3.1 | 6.3 | 25 |

The above data show that compound 11 (BB-K186) is equal to or superior in most respects to butirosin A and 4'-deoxybutirosin A in its activity against a variety of diseases organisms. It is particularly improved in its activity against Pseudomonas aeruginosa. In most instances, it is 2 to 4 fold as active as butirosin A, and in some instances 8 to 30 times as active.

Compound 11 is valuable as an antibacterial agent, nutritional supplement in animal feeds, therapeutic agent in poultry and animals, including man, and are especially valuable in the treatment of infectious diseases caused by Gram-positive and Gram-negative bacteria.

Compounds 11 when administered orally is useful as an adjunctive treatment for preoperative sterilization of the bowel. Both aerobic and anaerobic flora which are suseptible to this drug is reduced in the large intestine. When accompanied by adequate mechanical cleansing, it is useful in preparing for colonic surgery.

The novel medicament provided by the present invention may be formulated as pharamceutical compositions comprising, in addition to the active ingredient, a pharmaceutically acceptable carrier or diluent. The compound may be administered both orally and parenterally. The pharmaceutical preparation may be in solid form such as capsules, tablets, or dragees, or in liquid form such as solutions, suspensions or emulsions. In the treatment of bacterial infections in man, the compound of this invention may be administered parenterally in an effective amount of from about 250 mg. to about 3000 mg. per day in divided doses three or four times a day. Generally the compound is effective when administered at a dosage of about 5.0 to 7.5 mg./kg. of body weight every 12 hours. Thus, it is administered in man in dosage units containing, e.g. 125, 250 or 500 mg. of active ingredient with suitable physiologically acceptable carriers or excipients.

DESCRIPTION OF THE PREFERRED EMBODIMENTS

EXAMPLE 1

Tetra-N-benzyloxycarbonylbutirosin A (2)*

To a stirred mixture of 19.5 g. (35 mmoles) of butirosin A (1) and 8.20 g. (77.3 mmoles) of $Na_2CO_3$ in 440 ml. of 20% aqueous acetone was added dropwise 26.2 g. (153 mmoles) of benzyl chloroformate under cooling. The reaction mixture was stirred overnight at room temperature to give an oily precipitate, which was separated from the supernatant by decantation, washed thoroughly with water and triturated with ether to give 34.23 g. (89%) of 2.

*T. B. Culbertson, D. R. Watoson and T. H. Haskell, J. Antibiot. 26, 790 (1973).

EXAMPLE 2

Tetra-N-benzyloxycarbonyl-3',4';3'',5''-di-O-isopropylidenebutirosin A (4)

A solution of 14.3 g. (13.1 mmoles) of 2, 30 ml. of 2,2-dimethoxypropane and 60 mg. of p-toluenesulfonic acid in 250 ml. of DMF (dimethylformamide) was allowed to stand at room temperature for 2 days, then evaporated in vacuo to remove the MeOH formed. The concentrate was treated with another 10 ml. of 2,2-dimethoxypropane, kept at 60°C. for 2 hours, treated with about 1 ml. of $Et_3N$ and evaporated to dryness in vacuo. The oily residue was chromatographed on a silica gel column (180 g.) and eluted with $CHCl_3$-MeOH to give 5.5 g. (36%) of the diacetonide 4 and 8.45 g. (57%) of the monoacetonide 3*. Repeated isopropylidenation of 3 gave additional amount of 4. Total yield of 4 was 11.0 g. (72%). Monoacetonide (3), m.p. 123°–125°C.:

* Structure of 3 (monoacetonide)

Anal. Calcd. for $C_{56}H_{69}N_5O_{20}\cdot\frac{1}{2}H_2O$: C, 58.93; H, 6.18; N, 6.14. Found: C, 58.98; H, 5.99; N, 6.09. Diacetonide (4), m.p. 121°–123°C.:

Anal. Calcd. for $C_{59}H_{73}N_5O_{20}$: C, 60.54; H, 6.28; N, 5.97. Found: C, 60.44; H, 6.26; N, 5.79.

*Structure of 3 (monoacetonide)

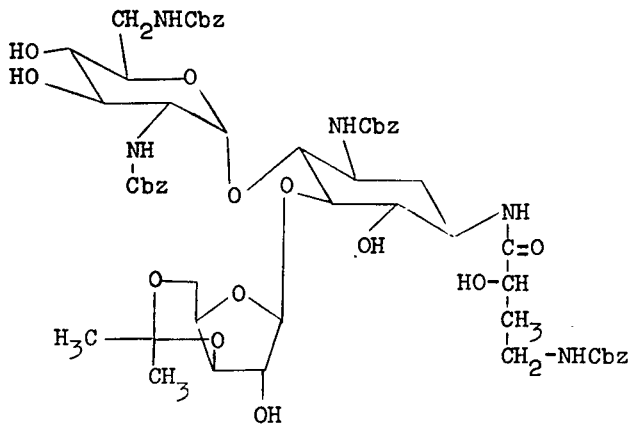

EXAMPLE 3

2'',6,α-Tri-O-acetyl-tetra-N-benzyloxycarbonyl-3',4'; 3'',5''-di-O-isopropylidenebutirosin A (5)

To a solution of 226 mg. (0.193 mmoles) of 4 in 10 ml. of dry pyridine was added 1.5 ml. of Ac₂O. The reaction mixture was allowed to stand overnight and poured onto ice-water. The mixture was extracted with CHCl₃. The CHCl₃ extracts were washed with water, dried with Na₂SO₄ and evaporated in vacuo to give 248 mg. (99%) of 5. An analytical sample was obtained by chromatography on silica gel; m.p. 108°–110°C.

Anal. Calcd. for $C_{65}H_{79}N_5O_{23}$: C, 60.13; H, 6.13 N, 5.39. Found: C, 60.09; H, 6.09; N, 5.44.

EXAMPLE 4

2'',6,α-Tri-O-acetyl-tetra-N-benzyloxycarbonyl-butirosin A (6)

A solution of 2.0 g. (1.54 mmoles) of 5 in 15 ml. of 80% aqueous acetic acid and 15 ml. of acetone was heated at 80°C. for 3 hours and then evaporated to dryness in vacuo. The residue was chromatographed on a silica gel column (62 g.) with CHCl₃-MeOH as eluent to give 1.55 g. (81%) of 6; m.p. 105°–106°C.

Anal. Calcd. for $C_{59}H_{71}N_5O_{23}$: C, 58.17; H, 5.87; N, 5.73. Found: C, 58.49; H, 6.18; N, 5.80.

EXAMPLE 5

2'',6,α-Tri-O-acetyl-tetra-N-benzyloxycarbonyl-3'',5''-O-isopropylidenebutirosin A (7)

To a solution of 1.82 g. (1.49 mmoles) of 6 in 24 ml. of dry DMF were added 24 ml. of 2,2-dimethoxypropane and 8 mg. of p-toluenesulfonic acid. The reaction mixture was allowed to stand overnight at room temperature, then treated with 0.1 ml. of Et₃N, and evaporated to dryness in vacuo. The residue was purified on a silica gel column (30 g.) with CHCl₃-MeOH to give 1.79 g. (96%) of 7; m.p. 105°–107°C.

Anal. Calcd. for $C_{62}H_{75}N_5O_{23}$: C, 59.18; H, 6.01; N, 5.57. Found: C, 59.37; H, 5.98; N, 5.41.

EXAMPLE 6

2'',6,α-Tri-O-acetyl-tetra-N-benzyloxycarbonyl-3'',5''-O-isopropylidene-3'-O-tosylbutirosin A (8)

To a stirred solution of 1.2 g. (0.955 mmoles) of 2'',6,α-tri-O-acetyl-tetra-N-benzyloxycarbonyl-3'',5''-O-isopropylidenebutirosin A (7) in 15 ml. of dry pyridine was added 900 mg. (4.72 mmoles) of tosyl chloride below −10°C. The reaction mixture was stirred for 2 days at room temperature and, after adding 10 ml. of water, evaporated to dryness in vacuo. The residue was triturated with water and dried in vacuo to yield 1.297 g. of crude 8, which was purified on a silica gel column (210 g.) with CHCl₃—MeOH system to give 641 mg. (48%) of 8; m.p. 105°–106°C. IR (KBr): $\nu_{SO_2}$ 1175 cm⁻¹.

Anal. Calcd. for $C_{69}H_{81}N_5O_{25}S$: C, 58.67; H, 5.78; N, 4.96; S, 2.27. Found: C, 58.83; H, 5.68; N, 4.77; S, 2.25.

EXAMPLE 7

3'-Deoxybutirosin A. BB-K186 (11)

7A.: A mixture of 282 mg. (0.2 mmoles) of 8, 520 mg. of NaI and 10 ml. of dry acetone in a sealed glass tube was heated at 120°–130°C. for 2 days, during which time crystals of sodium tosylate precipitated. The reaction mixture being filtered, the filtrate was evaporated to dryness in vacuo to leave an oily residue, which was washed with water and dried to give the 4'-iodo derivative (9) showing no $\nu_{SO_2}$ band in its ir spectrum. 7B.: A solution of the iodo derivative in 10 ml. dioxane was hydrogenated with 5 ml. of Raney nickel (a thick suspension in dioxane) and hydrogen at 42 psi for 2 days in a Paar hydrogenator. The catalyst was removed by filtration and the filtrate was repeatedly hydrogenated overnight with 5 ml. of Raney nickel. The reaction mixture was filtered and the filtrate was dried up in vacuo. The yellowish residue (152 mg.) was dissolved in 10 ml. of 10 % NH₃ in MeOH, allowed to stand for 1.5 hours at room temperature and then dried up in vacuo. The deacetylated product was dissolved in 10 ml. of 50% aqueous AcOH, heated at 80°C. for 2 hours and evaporated to dryness in vacuo to give 103 mg. of tetra-N-benzyloxycarbonyl-3'-deoxybutirosin (10). 7C.: A solution of 10 in 15 ml. of 50% EtOH was hydrogenated overnight with 100 mg. of 20% Pd-C and 0.1 ml. of Et₃N in a Paar apparatus at 42 psi. The catalyst was removed by filtration. The filtrate was evaporated to dryness in vacuo. The residue was chromatographed on a CG-50 column (NH₄⁺ form, 10 ml.) with 200 ml. of 0.1 N NH₄OH, 200 ml. of 0.2 N NH₄OH and 200 ml. of 0.5 N NH₄OH as eluent. Each 10 ml. fraction was collected. Fractions showing Rf 0.35 on TLC (developed twice with S-110 system*¹) were pooled, evaporated to dryness in vacuo and lyophilized to give 12 mg. (11% from 8) of 11.

*1 CHCl₃-MeOH-28% NH₄OH-H₂O (1 : 4 : 2 : 1)

Amberlite CG-50 is the tradename for the chromatographic grade of weakly acidic cationic exchange resin of a carboxylic-polymethacrylic type.

EXAMPLE 8

Preparation of the monosulfate salt of 3'-deoxybutirosin A (11)

One mole of 3'-deoxybutirosin A is dissolved in 1 to 3 liters of water. The solution is filtered to remove any undissolved solids. To the chilled and stirred solution is added one mole of sulfuric acid dissolved in 500 ml. of water. The mixture is allowed to stir for 30 minutes, following which cold ethanol is added to the mixture till precipitation occurs. The solids are collected by filtration and are determined to be the desired monosulfate salt.

EXAMPLE 9

Preparation of Disulfate Salt of 3'-deoxybutirosin A (11)

Thirty-five grams of 3'-deoxybutirosin A is dissolved in 125 ml. of deionized water. The pH is adjusted to 7-7.5 with 50% V/V sulfuric acid.

Eight and one half grams of Darco G-60 (activated charcoal) is added and the mixture is slurried at ambient room temperature for 0.5 hour. The carbon is removed by suitable filtration and washed with 40 ml. of water. The water wash is added to the filtrate.

The combined filtrate-wash above is adjusted to pH 2–2.6 with 50% V/V sulfuric acid.

Eight and one half grams of Darco G-60 is added to the solution. The mixture is slurried for 0.5 hour at ambient room temperature. The carbon is removed by suitable filtration and washed with 35 ml. of deionized water. The water is added to the filtrate.

The combined filtrate-wash is adjusted to pH 1–1.3 with 50% V/V sulfuric acid. This solution is added with rapid stirring over a 10 minute period to 600–800 ml. of methanol (3–4 volumes of methanol). The mixture is stirred for 5 minutes at pH 1–1.3, passed through a 100 mesh screen, stirred for 2 minutes and allowed to settle for 5 minutes. Most of the supernatant is decanted. The remaining slurry is suitably filtered, washed with 200 ml. of methanol and vacuum dried at 50°C. for 24 hours to yield the desired disulfate salt of 11.

EXAMPLE 10

3'-Deoxybutirosin A

Substitution in the procedure of Example 7, in step 7A, for the sodium iodide used therein of an equimolar quantity of lithium bromide produces the compound having the formula

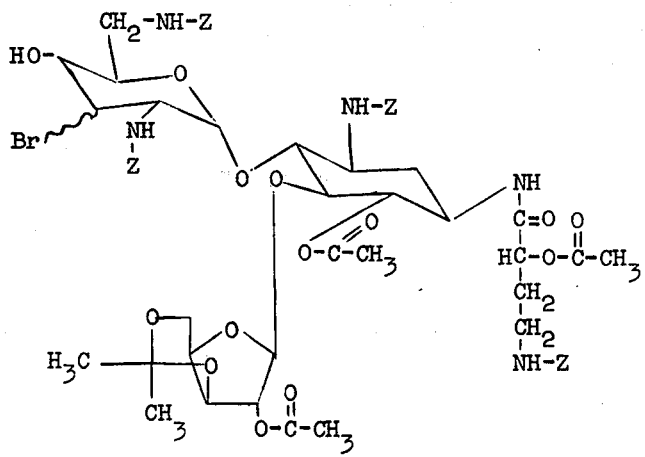

EXAMPLE 11

Alternative preparation of 3'-deoxybutirosin A, BB-K186 (11)

Step A — To a solution of 144 mg. of 2'',6,α-tri-O-acetyl-tetra-N-benzyloxycarbonyl-3'',5''-O-isopropylidene-3'-O-tosylbutirosin A (8) in 10 ml. of dry acetone was added 230 mg. of potassium thiolacetate and the mixture was heated in a sealed tube at 120°C. overnight. The sealed tube was cooled to room temperature and opened. The reaction mixture was filtered and the filtrate was evaporated in vacuo to dryness. The oily residue was triturated with water to give 121 mg. of the 3'-acetylthio derivative (12) which was purified by a column of silica gel (10 g.).

Step B — A solution of the 3'-acetylthio derivative in 5 ml. of dioxane was treated with 3 ml. of Raney nickel (a thick suspension in dioxane) and the mixture was refluxed for 3 hours. The reaction mixture was filtered and the filtrate was evaporated in vacuo to dryness. The residue was dissolved in 30 ml. of 10% ammonia in methanol and kept to stand at room temperature overnight. The reaction mixture was evaporated in vacuo to dryness and the residue was heated at 80°C. for 1 hour with 25 ml. of a mixture of 20% aqueous acetic acid and acetone (1 : 1) to afford tetra-N-benzyloxycarbonyl-3'-deoxybutirosin (10), which was identical with the authentic sample prepared by iodination of 8 followed by hydrogenation with Raney nickel.

Step C — A solution of 10 in 10 ml. of 60% aqueous ethanol was hydrogenated in the presence of 100 mg. of 20% Pd-C to give 5 mg. of BB-K186 (11), which was identical with the authentic sample from Example 7.

We claim:

1. The compound having the formula

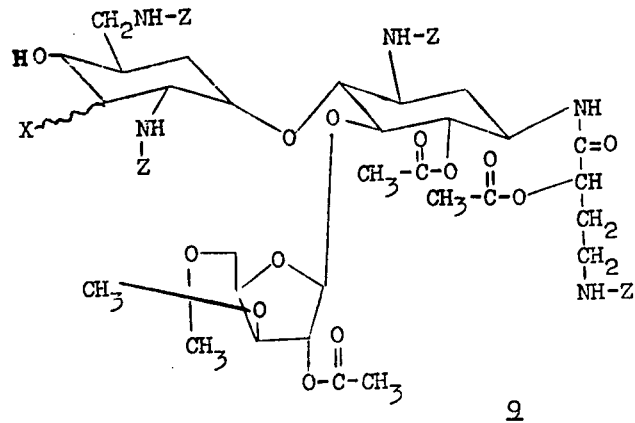

in which Z is a radical having the formula

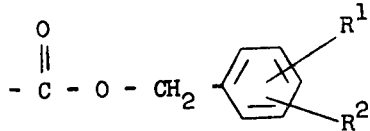

in which $R^1$ and $R^2$ are alike or different and each are hydrogen, chloro, bromo, fluoro, hydroxy, nitro, $CF_3$, $SO_3H$, (lower)alkyl of 1 to 3 carbon atoms or (lower)alkoxy of 1 to 3 carbon atoms and X is iodo, bromo or acylthio.

2. The compound of claim 1 in which Z is

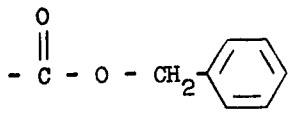

and X is iodo.

* * * * *